United States Patent [19]

Lim et al.

[11] Patent Number: 4,961,746

[45] Date of Patent: Oct. 9, 1990

[54] INTRAOCULAR LENS WITH COLORED LEGS AND METHOD OF MAKING

[75] Inventors: Drahoslav Lim, San Diego, Calif.; Stephen Jacoby, Belleair, Fla.; Richard Homick, San Diego, Calif.; Frank Powers, Clearwater, Fla.

[73] Assignee: American Cyanamid Company, Stamford, Conn.

[21] Appl. No.: 231,116

[22] Filed: Aug. 11, 1988

Related U.S. Application Data

[63] Continuation of Ser. No. 85,662, Aug. 5, 1987, abandoned, which is a continuation of Ser. No. 768,902, Aug. 23, 1985, Pat. No. 4,687,485.

[51] Int. Cl.[5] .............................................. A61F 2/16
[52] U.S. Cl. .......................................... 623/6; 264/1.7
[58] Field of Search ............................. 623/6; 264/1.7

[56] References Cited

U.S. PATENT DOCUMENTS

| 3,034,403 | 5/1962 | Neefe | 623/6 X |
| 3,454,332 | 7/1969 | Siegel | 264/1.7 X |
| 4,676,791 | 6/1987 | LeMaster et al. | 623/6 |
| 4,781,717 | 11/1988 | Grendahl | 623/6 |

FOREIGN PATENT DOCUMENTS

WO83/01568  5/1983  PCT Int'l Appl. ............. 623/6

OTHER PUBLICATIONS

The Rayner Choyce Mark VIII Anterior Chamber Implant, Catalogue No. 469, Rayner & Keeler Limited, (3 pages).

Primary Examiner—Ronald Frinks
Attorney, Agent, or Firm—David A. Warmbold

[57] ABSTRACT

An intraocular lens of the type having a plurality of legs which enter the lens in the anterior or posterior chamber by tangential contact between eye tissue and a region on each leg, wherein the region is composed of a compressible material. Also disclosed are homogeneous lenses in which the legs are colored.

23 Claims, 2 Drawing Sheets

INTRAOCULAR LENS WITH COLORED LEGS AND METHOD OF MAKING

This application is a continuation of our prior copending application Ser. No. 085,662, filed Aug. 5, 1987, now abandoned, which was a continuation of prior copending application Ser. No. 768,902, filed Aug. 23, 1985, now U.S. Pat. No. 4,687,485.

BACKGROUND OF THE INVENTION

The present invention relates to intraocular lenses, and in particular to intraocular lenses for placement in the anterior or posterior chamber of an eye following removal of the natural lens.

In several designs of intraocular lenses that are described in issued U.S. patents, the legs for centering the lens body work through tangential contact between a portion of the leg and the tissue of the eye. For instance, in some posterior chamber lenses, a portion of each leg tangentially contacts the ciliary body, which is the cleft at the intersection of the iris and the posterior capsule. In some anterior lenses, a portion of each leg tangentially contacts the junction between the cornea and the iris. For purposes of this invention, contact is considered "tangential" so long as the leg portion in question has the same geometrical slope as the tissues in contact with the leg portion. Thus, tangential contact within this definition is considered to include not only contact at one point, but also contact along a substantial length of the eye tissue where the curvature of the leg corresponds very closely to the curvature of the tissue. Lenses of this type having filamentary legs are described in U.S. Pat. No 4,477,931 to Kelman, U.S. Pat. No. 4,468,820 to Uhler, et al., U.S. Pat. No. 4,435,855 to Pannu, U.S. Pat. No. 4,418,431 to Feaster, and U.S. Pat. No. 4,159,546 to Shearing. Lenses of this type having legs which are non-filamentary, i.e. comprising a pair of tabs or equivalent means, are described in U.S. Pat. No. 4,414,694 to Choyce, for example.

Leg means of this type necessarily exert some force against the eye tissues in order to hold the lens in position. The force is alleviated somewhat by various configurations of the leg, between the region which contacts the eye tissues and the point at which the leg is attached to the lens body, or by providing that the leg can lie in a plane which is parallel to and/or offset from the plane of the lens body. However, since there must still be force applied to the eye tissues, which can provide discomfort and/or trauma to the tissues, it is desirable to provide further relief.

Another problem encountered in this field is that lenses made entirely of clear material are difficult to work with because they are difficult for the practitioner to see before, during and after implantation in the eye. Thus, there is a need for a lens which has colored leg means, without having to mold colored legs separately and then attach them in some manner to the lens body.

SUMMARY OF THE INVENTION

One aspect of the present invention comprises an intraocular lens for placement in the anterior or posterior chamber of the eye, comprising (a) a lens body; and (b) leg means, attached to said lens body and comprising a plurality of legs, for centering said lens body in the anterior or posterior chamber by tangential contact between eye tissue at the periphery of said posterior chamber and a region on the outer periphery of each leg, wherein each of said regions is composed of a compressible material.

In another aspect of the invention, an intraocular lens having a lens body and leg means integral with the lens body for centering the lens body in the anterior or posterior chamber of the eye is characterized in that the lens body is clear, and the leg means and optionally also the periphery of the lens body are colored.

DETAILED DESCRIPTION OF THE INVENTION

Figure 1:
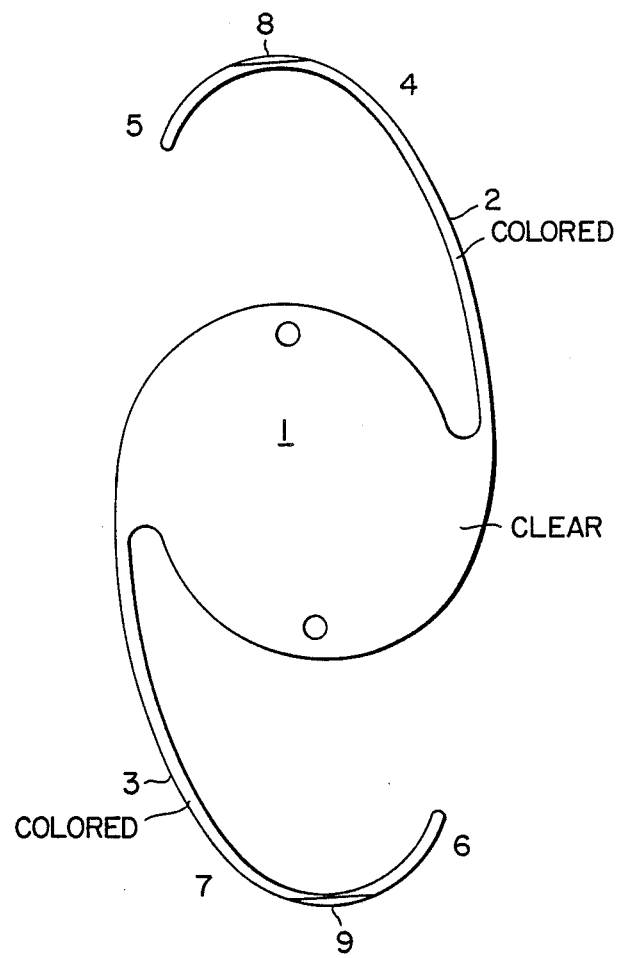
FIG. 1 is a top plan view of one embodiment of the intraocular lens of the present invention wherein the lens body is clear and the leg means are colored.

The present invention is useful with lenses having many different leg configurations, filamentary or non-filamentary, by which is meant solid tab-like projections that engage the supporting tissues of the eye. Filamentary legs include legs having one free end and one end attached to the lens body, such as the J-shaped loops disclosed in U.S. Pat. No. 4,159,546 to Shearing. They also include legs both of whose ends are attached to the lens body, thereby forming a loop; there can be one, two, three, four or more such legs or loops. There can be two, three, four or more tab-like non-filamentary legs.

For exemplification purposes, two such lenses are depicted in the accompanying Figures and will be discussed herein. Referring to both FIGS. 1 and 2, the lens includes lens body 1 to which are attached legs 2 and 3. Each leg includes a region which contacts the eye tissue. On leg 2, the region is designated as 8 between points 4 and 5; on leg 3, the region is designated as 9 between points 6 and 7. Regions 8 and 9 thus comprise the part of the leg structure which is at the periphery which touches the eye tissue. In a posterior chamber lens, the eye tissue is in the ciliary body or the capsular bag; in an anterior chamber lens, the eye tissue is at the junction of the cornea and iris.

The lens body and legs 2, 3 should be made of physiologically inert material which provides resiliency to the legs and from which a clear, transparent, refractive lens body can be fashioned. The lens body and legs 2, 3 can be made of polymethylmethacrylate ("PMMA") or of copolymers of methylmethacrylate with polyfunctional cross-linking agents such as ethylene glycol dimethacrylate ("EGDMA"). The lens body and legs are preferably cast all in one piece, or the legs can be molded separately and then fused or glued and staked into small holes provided for that purpose in the lens body. The lens body can optionally contain a small but effective amount of an ultraviolet-absorbing compound, such as any of the "Tinuvin P" family of commercially available benzotriazole derivatives and other commercially available similar benzotriazole derivatives.

Other effective UV absorbing compounds include "Permasorb" and other commercially available similar hydroxy benzophenone derivatives. Derivatives of both the benzotriazole and the hydroxy benzophenone type of ultraviolet radiation absorber are also commercially available which incorporate olefinic double bonds into part of the structure of the molecule of such absorbing compound. These olefinic double bonds, whether of an acryl, methacryl, vinyl or other type known to the art convert the UV absorber into a monomer which chemically bonds into the polymers of this invention. The use of such UV absorbing monomers is a preferred embodiment of the present invention.

Regions 8 and 9 are made of material which is compressible when the lens is in place in the eye. One satisfactory material for regions 8 and 9 is hydrophilic gels made from polymerized HEMA (2-hydroxyethyl methacrylate). Other suitable materials are polymers of 2,3-dihydroxypropylmethacrylate, and other hydrophilic amides and hydroxylated monomers and copolymers such as:

HEMA/N-vinyl pyrrolidone
2,3-dihydroxypropylmethacrylate/methylmethacrylate
HEMA/N-vinylpyrrolidone/methyl methacrylate
HEMA/methacrylic acid
HEMA/2-ethoxyethylmethacrylate
HEMA/methacrylic acid/isobutyl methacrylate.
hydroxypropylmethacrylamide/methyl methacrylate
dimethylacrylamide/diethyl acrylamide
HEMA/n-hexyl acrylate
HEMA/hydroxypropyl methacrylate The embodiments of this invention include, but are not limited to the above copolymers.

It will be recognized that cross-linking agents such as ethylene glycol dimethacrylate or other bifunctional and polyfunctional monomers well known to the art may be added to these monomers in amounts in the range of 0–5% to cause the resultant copolymer to become a gel.

Other satisfactory materials which have the desired properties of compressibility (softness), ability to bond to PMMA, and physiological compatibility and inertness, will be apparent to those skilled in this art.

The regions 8, 9 can be, for example, about 0.005 inches thick, i.e. sufficient to impart the desired cushioning to the leg while preserving the resiliency of the leg itself necessary for ensuring that the lens is centered correctly. Other cushion thicknesses may be used depending upon specific lens designs.

Figure 2:
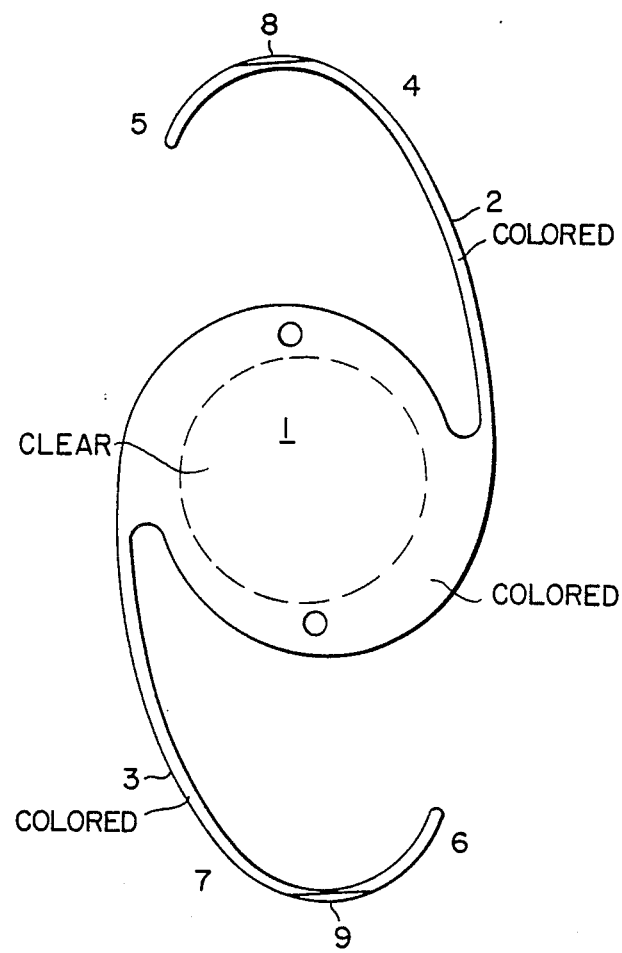
FIG. 2 is a top plan view of a second embodiment of the intraocular lens of the present invention wherein the central lens body is clear and the leg means and outer periphery of the lens body are colored.

The present invention also includes within its scope intraocular lenses, for placement in the posterior chamber, wherein the legs for centering the lens in the chamber are colored, e.g. blue, red, etc., as shown in FIG. 1. The periphery of the lens body itself can also be colored as shown in FIG. 2. In these lenses the legs are integral with the lens body, that is, made of the same material as the lens body and formed all in one piece with the lens body as polymerized, as distinguished from lenses in which colored legs are polymerized and thereafter glued or otherwise attached to the lens body. The lens body and the legs are preferably made of polymethylmethacrylate. If color is imparted around the outer edge of the lens body as shown in FIG. 2, it preferably does not extend closer than about 2–3 mm from the center; the center region of the lens body should remain clear to provide unimpeded vision to the wearer. Color can be imparted by incorporating into the part to be colored any physiologically compatible dye; a satisfactory dye is D+C Green #6, which despite its name provides a blue color in situ.

The colored legs can also be provided with soft compressible regions as described herein.

Discs having structures suitable for lathe-cutting into the intraocular lenses of this invention, can be made by a procedure which begins with polymerizing in a tubular mold a liquid mixture of initiator and monomer or comonomer as previously described for forming an optically clear lens body. The ultraviolet absorbing compounds previously described may be added to the lens body monomers prior to polymerization and incorporated into the resultant polymer. The polymer rods produced by these means are then lathe cut to a radius 0.1–1.0 mm less than the distance from the center of the lens body to the interface between the compressible material and the eye tissue which the compressible material will contact. The resultant rods are then precisely mounted in the center of a cylindrical tubular mold and mixtures of initiator and monomers, previously described as suitable for forming the polymer of the compressible material, are added and polymerized to form a cylindrical ring around the rod of the polymer used to form the lens body and most or all of the legs of the lens. The resultant rod is then lathe cut to a radius 1.0–3.0 mm more than the distance from the center of the lens body to the farthest edge of the legs. This rod is then sawed or otherwise cut into discs of uniform thickness, suitable for lathe cutting and machine milling in the conventional manner into the intraocular lens of the present invention, as previously described.

To form an integral intraocular lens having colored legs, methylmethacrylate, or a polymer of other monomers or comonomers usable to form the lens body is polymerized in a tube by the methods described above and lathe cut to the same radius as the desired lens body. This rod is then centered in a tube and a solution of the initiator, monomers and dye suitable for forming the material of the colored legs is poured into the tube and polymerized by means previously described for forming a region of compressible materials on a rod of optically clear polymer The rough surface of the outer cylindrical ring of colored material is lathe cut away to a depth of at least about 1.0 mm below the original circumference of the two-layered rod, leaving a thickness of colored polymer sufficient to form the colored legs of the resultant intraocular lens.

Further, if a region of compressible material is desired on the outer edge of the colored legs, then the procedure previously described for casting a layer of this polymer on a rod of optically clear polymer may be identically repeated on the rod having an outer ring of colored material.

All rods produced by these means can then be cut into discs which can be lathe cut and machined by the conventional means used to form an intraocular lens.

Materials, and amounts thereof, to use as initiator are well-known in this art. One satisfactory initiator is a mixture of tert-butyl peroctoate and tert-butyl perneodecanoate (which are commercially available as "Esperox 33" and "Esperox 28" respectively). This mixture is added in an amount up to about 0.5 wt. %.

EXAMPLE 1

A liquid mixture of the following compounds was prepared in the indicated proportions: 995 parts by weight of methyl methacrylate, 5 parts ethylene glycol dimethacrylate, 2 parts methoxy benzoin, and 2 parts Esperox 33. It was added to an 18 mm×115 mm polypropylene test tube and sealed in using a rubber septum secured by a plastic clamp. Pure nitrogen was rapidly bubbled through the monomers for 15 minutes using a long syringe needle that pierced the septum and reached the bottom of the tube (with a short needle also piercing the septum to vent the displaced air). This flushed all oxygen from the monomer in order to eliminate its interfering with the polymerization.

The tube was then sealed air tight and exposed to a source of ultraviolet radiation of uniform but low intensity for a period of 24 hours. The rods were rotated 120° every 8 hours to assure uniform exposure of all parts of the polymerizing mixture to the UV radiation, which provides the energy to initiate polymerization. After this treatment the polymer rod was post-cured by incubating it at 60° C. for 24 hours to ensure completion of polymerization. The polymer rod obtained was mounted in a lathe and cut precisely to a diameter of 13.50±0.05 mm.

The rod was carefully cleaned to remove any adherent oils or grease deposited by the lathe cutting and subsequent handling, using Freon MF or TF as degreasing solvent. The rod was dried in air at 50° C. for 4 hours and then mounted in the exact geometric center of a test tube (other suitable equivalent tubing made of Teflon, polyethylene, polypropylene or silylated glass can be used). A mixture consisting of 800 parts by weight of hydroxyethyl methacrylate, 200 parts n-hexyl acrylate, 5 parts ethylene glycol dimethacrylate, and 2 parts Esperox 33 was added to the tube, which was then sealed air tight and flushed with nitrogen gas, as was previously described for the polymerization of the monomers for the core rod. The rods were then cured in an air convection oven thermostated at 60°±2° C. for 24 hours and then post cured at 95° C. for 4 hours to assure complete decomposition of all peroxides.

The resultant rod with a two layered polymer structure was removed from the tube and precisely mounted in a lathe in order to turn the rod about the geometrical center of the original rod that forms the core of the two layered rod. The polymer forming the outer layer was then lathe cut away down to a diameter of 16.00±0.05 mm. A 5 mm length was then trimmed from both ends of the double layered structure of the rod and the remaining central portion of the shaft sawed into discs 3.0±0.1 mm thick.

These discs were then cut to produce intraocular lenses having the leg configuration illustrated on the attached drawing. The objects produced from this operation were next hydrated by soaking in a 0.9% sodium chloride and water solution for three days. The result was an intraocular lens having a rim of polymer on the outer side of the legs which proves to be soft and rubbery but strongly adherent to the rest of the leg.

EXAMPLE 2

Another core rod was prepared from the same composition of monomers described in Example 1 by the same procedure described in Example 1 except that it was lathe cut to a smaller diameter of 7.50±0.05 mm. This rod was cleaned, degreased and dried, and then precisely centered in a polypropylene tube having a 20 mm diameter all using techniques identical to those described in Example 1. To this tube was added a mixture, consisting of 990 parts by weight of methyl methacrylate, 10 parts ethylene glycol dimethacrylate, 2 parts Esperox 33, 2 parts Esperox 28, and 0.50 parts of D&C Green No. 6 dye. The tube was next sealed and flushed with nitrogen gas as previously described. It was next cured by immersing the tubes in a thermostated water bath, set at 50°±2° C. for another 24 hours, with a post cure at 95° C. for 4 hours. The resultant rod was next trimmed and lathe cut to a 16.00 mm diameter as described previously and then sawed into discs 3.0±0.1 mm thick. These discs were then cut to produce lenses as in Example 1. The resultant object was an intraocular lens, the legs of which, however, were a blue color of moderate intensity. When this lens is immersed in water the legs of this lens are much more easily visible than the legs of similar lenses having clear, uncolored legs.

What is claimed is:

1. An intraocular lens adapted for implantation in the anterior chamber of the eye, comprising a lens body and leg means, formed with said lens body and comprising a plurality of legs, for centering said lens body in said chamber, wherein said legs are polymerized to said lens body and are colored and at least a portion of said lens body is clear, the colored portions of said legs and lens body being colored before polymerization to the lens body.

2. An intraocular lens adapted for implantation in the posterior chamber of the eye, comprising a lens body and leg means, formed with said lens body and comprising a plurality of legs, for centering said lens body in said chamber, wherein said legs are polymerized to said lens body and are colored, and at least a portion of said lens body is clear, the colored portions of said legs and lens body being colored before polymerization to the lens body.

3. The lens of claim 1 wherein said lens body and legs are made of polymethylmethacrylate.

4. The lens of claim 2 wherein said lens body and legs are made of polymethylmethacrylate.

5. The lens of claim 1 wherein the periphery of said lens body is colored.

6. The lens of claim 2 wherein the periphery of said lens body is colored.

7. An intraocular lens for implantation in the eye comprising:
   (a) a lens body and leg means formed with said lens body and comprising a plurality of legs, the lens body and leg means being formed from a rod having a central zone and a peripheral zone;
   (b) the central zone being formed by polymerizing an optically clear material suitable for use in the eye to provide the clear lens body; and
   (c) the peripheral zone being formed by polymerizing a material, suitable for use in the eye and having a colored dye mixed therein, to the central lens body to provide the colored leg means.

8. The lens of claim 7 wherein the leg means comprises a plurality of legs extending from the lens body such that the lens body is clear and the plurality of legs are colored.

9. The lens of claim 8 wherein the leg means comprises a peripheral portion surrounding the central lens body and a plurality of legs extending from the peripheral portion such that the central lens body is clear and the peripheral portion and plurality of legs are colored.

10. A process for making an intraocular lens comprising a clear lens body and colored legs integral with said lens body for supporting the lens within the anterior or posterior chamber of the eye, comprising:
   (a) forming a clear rod out of a physiological inert material including a polyfunctional cross-linking agent and having the diameter of the lens body;
   (b) positioning said rod in a tubular mold and forming around said rod an annular layer of a polymerizable liquid solution of the same physiological inert material of step (a), or copolymer thereof, and with or without a polyfunctional cross-linking agent and containing a dye;

(c) polymerizing said polymerizable solution to form a one-piece rod and annular layer having a clear center portion and a colored outer portion; and (d) machining said rod with said annular layer to produce therefrom said intraocular lens with a clear lens body and colored legs.

11. The process of claim 10 wherein said physiological inert material is polymethylmethacrylate (PMMA).

12. The process of claim 10 wherein said physiological inert material is a copolymer of methylmethacrylate.

13. The process of claim 10 wherein said polyfunctional cross-linking agent is ethylene glycol dimethacrylate.

14. The process of claim 10 wherein step (d) comprises cutting a disc from said rod with said annular layer, and removing material from said annular layer to form the legs and removing material from said clear rod to form said clear lens body.

15. The process of claim 10 wherein said dye is D and C Green No. 6.

16. An intraocular lens produced by the process of claim 10.

17. A process for making an intraocular lens comprising a partially clear lens body and colored legs integral with said lens body for supporting the lens within the anterior or posterior chambers of the eye, comprising:

(a) forming a clear rod out of a physiological inert material including a polyfunctional cross-linking agent;

(b) positioning said rod in a tubular mold and forming around said rod an annular layer of a polymerizable liquid solution of the same physiological inert material of step (a), or copolymer thereof, and with or without a polyfunctional cross-linking agent and containing a dye;

(c) polymerizing said polymerizable solution to form a one-piece rod and annular layer; and (d) machine said rod and annular layer to produce therefrom said intraocular lens having a partially clear body and colored legs.

18. The process of claim 17 wherein said physiological inert material is polymethylmethacrylate (PMMA).

19. The process of claim 17 wherein said physiological inert material is a copolymer of methylmethacrylate.

20. The process of claim 17 wherein said polyfunctional cross-linking agent is ethylene glycol dimethacrylate.

21. The process of claim 17 wherein step (d) comprises cutting a disc from said rod with said annular layer, and removing material from said annular layer to form the legs and removing material from said clear rod and annular layer to form said partially clear lens body.

22. The process of claim 17 wherein said dye is D and C Green No. 6.

23. An intraocular lens produced by the process of claim 17.

* * * * *